United States Patent [19]
Karami et al.

[11] Patent Number: 5,263,949
[45] Date of Patent: Nov. 23, 1993

[54] DISPOSABLE DIAPER WITH BARRIER SHEET

[75] Inventors: Hamzeh Karami, Mansfield; Ronald F. Vitaris, Worcester, both of Mass.

[73] Assignee: The Kendall Company

[21] Appl. No.: 454,220

[22] Filed: Dec. 21, 1989

Related U.S. Application Data

[63] Continuation-in-part of Ser. No. 406,020, Sep. 12, 1989.

[51] Int. Cl.⁵ .............................................. A61F 13/15
[52] U.S. Cl. ................................. 604/383; 604/358; 604/385.1
[58] Field of Search .................. 604/385.2, 381, 378, 604/358, 385.1

[56] References Cited

U.S. PATENT DOCUMENTS

| | | | |
|---|---|---|---|
| 3,838,693 | 10/1974 | Sherman | 604/378 |
| 3,949,130 | 4/1976 | Sabee | 604/378 |
| 4,410,324 | 10/1983 | Sabee | 604/385.2 |
| 4,480,000 | 10/1984 | Watanabe et al. | 604/385.1 |
| 4,579,556 | 4/1986 | McFarland | 604/385.2 |
| 4,636,209 | 1/1987 | Lassen | 604/378 |
| 4,699,620 | 10/1987 | Bernardin | 604/385.1 |
| 4,808,176 | 2/1989 | Kielpikowski | 604/386 |

Primary Examiner—David Isabella
Assistant Examiner—Rob Clarke
Attorney, Agent, or Firm—Alvin Isaacs

[57] ABSTRACT

A disposable diaper having a backing sheet having a crotch portion, an absorbent pad having a pair of opposed side edges, and a liquid impervious barrier sheet having side margins extending around the side edges of the pad, such that the barrier sheet provides a barrier preventing waste material from escaping through the back of the diaper or through the side edges of the pad.

7 Claims, 2 Drawing Sheets

DISPOSABLE DIAPER WITH BARRIER SHEET

CROSS REFERENCE TO RELATED APPLICATION

This application is a continuation-in-part of application, Ser. No. 406,020, filed Sep. 12, 1989.

BACKGROUND OF THE INVENTION

Disposable diapers for infants and incontinent people are a major industry, and, as such, constitute a crowded art, competitively speaking.

In general, they comprise an absorbent pad assembly having a liquid impervious backing sheet, an absorbent pad in a crotch portion of the diaper, and a liquid pervious cover or front sheet.

In general, the prior concepts for providing liquid impermeability suffer from the following deficiency: inability to prevent edge leakage through the side edges of the crotch area to soil the leg, clothing, bedsheet and/or other surrounding articles.

With respect to the latter, the prior art, as exemplified by the patent literature, also discloses the separate concept of providing barrier strips and the like along the edges to prevent this edge leakage. Illustrative patents providing such means for preventing edge leakage include U.S. Pat. Nos. 3,349,769 issued to Piekarski; 3,572,342 of Linquist et al.; 4,610,682 of Kopp; and 4,804,379 of Toth et al.

The present invention relates to a disposable diaper which prevents edge leakage in an improved manner, the diaper being characterized further as being of an elegant and cost effective design which permits the use of less expensive materials in the manufacture of the backing sheet.

SUMMARY OF THE INVENTION

In accordance with the present invention, a unitary disposable diaper is provided of per se known configuration, e.g. substantially rectangular or of an hourglass configuration, comprising a backing sheet in a crotch portion of the diaper and corner or wing portions surrounding the crotch portion, with the crotch portion having a liquid impervious barrier sheet carrying an absorbent pad of like dimensions for receiving and retaining body waste material, with side margins of the liquid impervious barrier sheet extending around opposed side edges of the pad and preferably being sealed over the front surface thereof, such that the barrier sheet prevents body waste material from escaping through the back of the diaper or leaking through the side edges.

DESCRIPTION OF THE PREFERRED EMBODIMENTS

Figure 1:
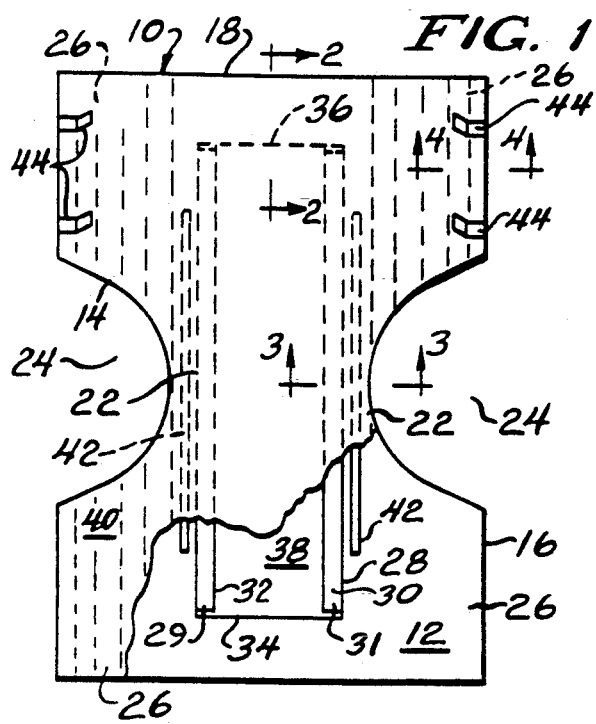
FIG. 1 is a top plan view, partly broken away, of a disposable diaper of the present invention.
Figure 2:
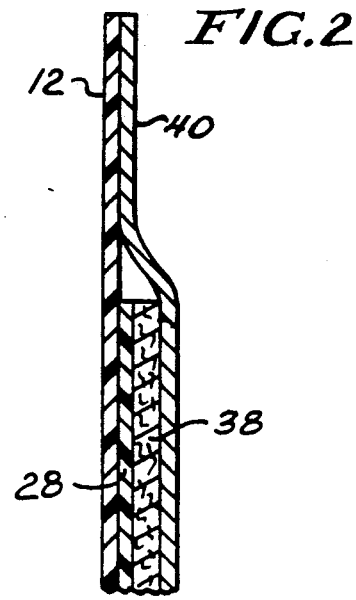
FIG. 2 is a fragmentary sectional view taken substantially as indicated along the line 2—2 of FIG. 1.
Figure 3:
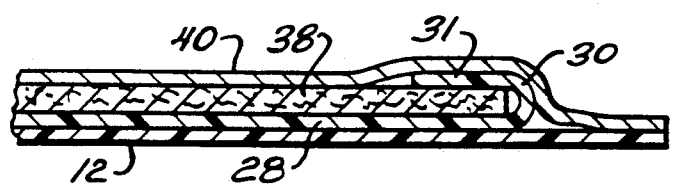
FIG. 3 is a fragmentary sectional view taken substantially as indicated along the line 3—3 of FIG. 1.
Figure 4:
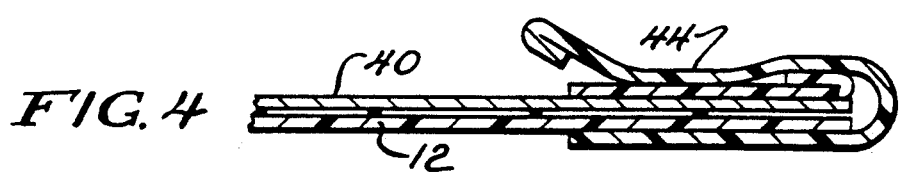
FIG. 4 is a fragmentary sectional view taken substantially as indicated along the line 4—4 of FIG. 1.

Referring now to FIGS. 1-4, a diaper 10 of the present invention has its periphery defined by a liquid impervious backing or back sheet 12 having opposed side edges 14 and 16, and a pair of opposed end edges 18 and 20 connecting the side edges 14 and 16.

The diaper 10 has a crotch portion 22, i.e. a portion adapted to engage the crotch area of the wearer to capture body waste material. While not essential to the practice of this invention, the diaper 10 is shown to have cut-out portions 24 on opposed sides of the crotch portion 22 such that the diaper has a generally hourglass configuration having four wings or ear portions 26 in the areas surrounding the crotch portion where the end edges connect with the side edges. When the diaper is folded medially to be put on the body, the wings 26 engage the waist and stomach areas. It will of course be appreciated that the configuration shown in the drawing for purposes of illustration is not critical, and other shapes or configurations will be a matter of individual choice within the expected judgment of the skilled worker.

Secured in fluid tight communication with the back sheet 12 in the crotch portion 22 is a liquid impervious barrier sheet 28 having a pair of opposed side margins 29 and 31 defining respective opposed side edges 30 and 32, and a pair of opposed end edges 34 and 36 connecting the side edges 30 and 32.

The diaper 10 has an absorbent pad 38 seated on an inner surface of the barrier sheet 28 for capturing and retaining body waste material. As shown, opposed side margins 29 and 31 of the barrier sheet 28 extend around and over the side edges of the pad 38. In this manner, edge leakage of body waste from the pad is precluded.

Preferably, a front or cover sheet 40 (shown partially broken away in FIG. 1 to reveal the underlying elements of the diaper) is also provided. The cover sheet 40, which is liquid pervious, is shown to be of substantially the same configuration and dimensions as the backing sheet 12 and the respective sheets are secured together at least around their common periphery. Preferably, the side margins and the barrier sheet 28 are sealed to a back surface of cover sheet 40 to assure a fluid-tight barrier against edge leakage from the absorbent pad, e.g. by heat sealing or by means of a pressure-sensitive adhesive. Alternately, they may be sealed directly to the front surface of the absorbent pad or indirectly through intermediate strips of sheet material adhered to the side edges of the absorbent pad.

A pair of elastic strips 42 are preferably provided on opposed side edges of the barrier sheet 28 in order to gather the crotch area 22.

A pair of conventional tape fasteners 44 in the waist area permit releasably securing or refastening the opposed end edges 18 and 20 together around the waist when the diaper is folded to engage the front and back of the body.

When a diaper of the foregoing general description is intended for infants, it may, for example, be on the order of from about 10″ to about 25″ in length and from about 10″ to about 17″ at its widest width, in which case the absorbent pad seated on barrier sheet 38 and sealed thereto along the side edges may be on the order of from about 8″ to about 23″ in length and from about 5″ to about 12″ in width. On the other hand, diapers intended for incontinent adults will of course be substantially larger. For example, the adult diaper may be on the order of from about 26″ to about 50″ in length and from about 18″ to about 40″ in width with pad 38 covering the crotch area on the order of from about 24″ to about 48″ in length and about 5″ to about 20″ in width.

The backing or back sheet 12, which may be on the order of 0.1 to 2.0 mils thick, may if desired comprise a flexible plastic such as a polyolefin, e.g. polyethylene or polypropylene, a polyester such as polyethylene terephthalate, or a cellulose ester such as cellulose acetate or triacetate.

The barrier sheet 28, which also may be on the order of from about 0.1 to about 1.5 mils thick, may comprise any of the impervious materials heretofore used for backing sheets, polyethylene or polypropylene being illustrative.

The pad 38 may comprise any of the absorbent materials heretofore employed in the diaper art, e.g. wood pulp or fluff, cellulose wadding, absorbent cotton fibers, polyester or polyolefin and the like, including mixtures thereof. As is known in the disposable diaper art, one or more layers containing a superabsorbent material may also be utilized.

The liquid pervious top sheet 40 likewise may comprise any of the materials heretofore employed for top sheets, e.g. spun bonded polyester or polyropylene fibers, various nonwoven fabrics, gauze, etc. having the requisite wet and dry strength.

The tape fasteners 44, which per se comprise no part of this invention, may be any of the known tape structures utilizing so-called refastenable pressure-sensitive adhesive, e.g. acrylic adhesive formulations or elastomeric adhesive formulations such as those of the KRATON series (trademark of Shell Chemical Company) which are styrene-isoprene block copolymers.

Elastic strips, such as strips 42, are also well known in the diaper art. They may comprise any elastomer such as natural, butyl, or synthetic rubber having the requisite tensile force to provide gather, e.g. 100 grams when stretched 100% from the relaxed condition. While shown in the illustrative drawing to comprise a single strand, a plurality of such strands are also contemplate.

In foregoing description, the backing sheet 12 has been shown to be a continuous film to which barrier sheet 28 is sealed on by heat or hot melt adhesives.

However, it will be appreciated that the portion in juxtaposition with the major portion of the barrier sheet 28 is superfluous and may accordingly be eliminated.

It is therefore contemplated that in lieu of the continuous surface area film, the backing sheet may have a central opening or window in the crotch area with the barrier sheet 28 sealed around the periphery over the window. In this context, it will of course be appreciated that the dimensions of the window should be slightly smaller than those of the barrier sheet 28, e.g. on the order of at least one inch in both length and width, thus leaving a border or peripheral edge of the window of, say, at least 0.5 inch to which the back of barrier sheet 28 may be sealed, for example, by heat sealing.

An important feature of the present invention is the fact that the absorbent pad 38 covers only the surface of the liquid impervious barrier sheet 28, as distinguished from those diapers of the prior art wherein the absorbent pad extends near the edges of the backing sheet. The barrier sheet 28 prevents escape of the body waste materials through the back and edges of the diaper.

While cover sheet 40 is shown to be of substantially the same configuration and dimensions as the back sheet, it is to be understood that it may only cover the absorbent pad, in which event it will be sealed around its periphery to the periphery of the barrier sheet 28 and/or to the back sheet just beyond the barrier sheet 28. Likewise, the back sheet may be narrower than the cover sheet.

From the foregoing description, it will be seen that the present invention provides an elegant design of simplified construction wherein body waste materials are effectively confined within the crotch area by means of the barrier sheet 28.

Figure 5:
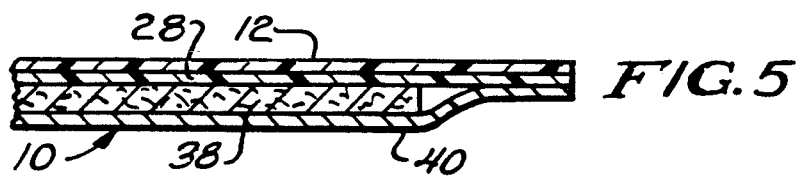
FIG. 5 is a fragmentary sectional view of another embodiment of the present invention.

FIG. 5 shows another embodiment of the diaper of the present invention, in which like reference numerals designate like parts. In this embodiment, the barrier sheet 28 extends to the end edges of the backing sheet 12 and cover sheet 40. In other respects, the diaper of FIG. 5 is similar to that previously discussed in connection with FIGS. 1–4.

Figure 6:
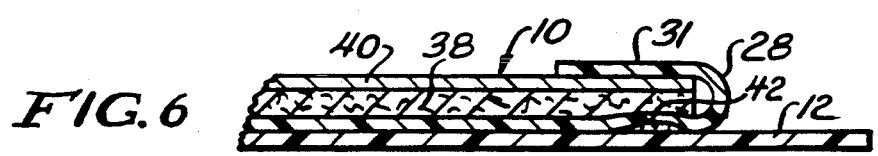
FIG. 6 is a fragmentary sectional view of another embodiment of the present invention.

Another embodiment of the diaper 10 of the present invention is illustrated in FIG. 6, in which like reference numerals designate like parts. In this embodiment, side margins 31 of the barrier sheet 28 are located over side margins of the cover sheet 40 at a location over a front surface of the absorbent pad 38. In addition, the elastic members or strips 42 are located intermediate the backing sheet 12 and barrier sheet 28 adjacent side edges of the pad 38.

Figure 7:
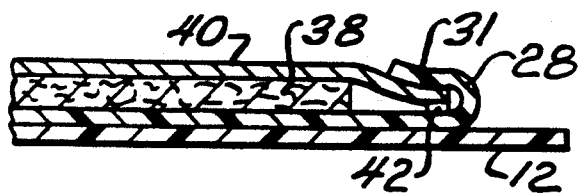
FIG. 7 is a fragmentary sectional view of another embodiment of the present invention.

Another embodiment of the diaper of the present invention is illustrated in FIG. 7, in which like reference numerals designate like parts. In this embodiment, side margins 31 of the barrier sheet 28 are adhered over side margins of the cover sheet 40, and the elastic strip 42 is located intermediate the cover sheet 40 and the barrier sheet 28 adjacent the side edges of the cover sheet 40. In other respects, the diaper of FIG. 7 is similar to that previously discussed in connection with FIGS. 1–4.

Figure 8:
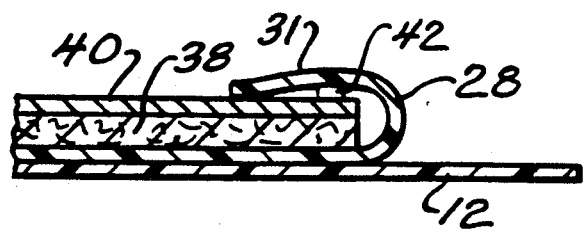
FIG. 8 is a fragmentary sectional view of another embodiment of the present invention.

Another embodiment of the diaper of the present invention is illustrated in FIG. 8, in which like reference numerals designate like parts. In this embodiment, the side margins 31 of the barrier sheet 28 are located over side margins of the cover sheet 40, and the elastic strips 42 are located intermediate the side margins 31 of the barrier sheet 28 and the side margins of the cover sheet 40. In other respects, the diaper of FIG. 8 is similar to that previously discussed in connection with FIGS. 1–4.

Figure 9:
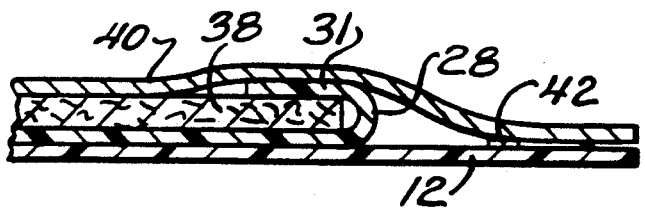
FIG. 9 is a fragmentary sectional view of another embodiment of the present invention.

Another embodiment of the diaper of the present invention is illustrated in FIG. 9, in which like reference numerals designate like parts. In this embodiment, the side edges of the cover sheet 40 are located adjacent side edges of the backing sheet 12, the elastic strip 42 is located intermediate the cover sheet 40 and backing sheet 12, and the cover sheet 40 and backing sheet 12 are adhered together adjacent side edges of the cover sheet 40 and backing sheet 12. In addition, the side margins 31 of the barrier sheet 28 extend over the front surface of the absorbent pad 38 at a location beneath the cover sheet 40. In other respects, the diaper of FIG. 9 is similar to that previously discussed in connection with the diaper of FIGS. 1-4.

Figure 10:
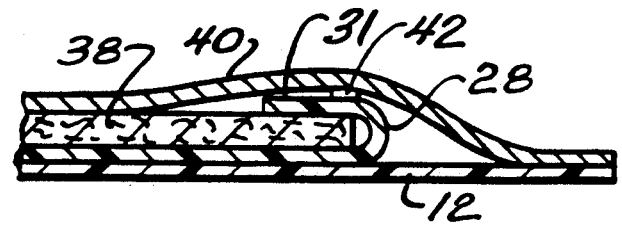
FIG. 10 is a fragmentary sectional view of another embodiment of the present invention.

Another embodiment of the diaper of the present invention is illustrated in FIG. 10, in which like reference numerals designate like parts. In this embodiment, the side margins 31 of the barrier sheet 28 are located over side margins of the absorbent pad 38 at a location beneath the cover sheet 40, and the side edges of the cover sheet 40 are located adjacent the side edges of the backing sheet 12. Also, in this embodiment, the elastic strips 42 are located intermediate the side margins 31 of the barrier sheet 28 and the cover sheet 40. In other respects, the diaper of FIG. 10 is similar to that previously described in connection with FIGS. 1-4.

Figure 11:
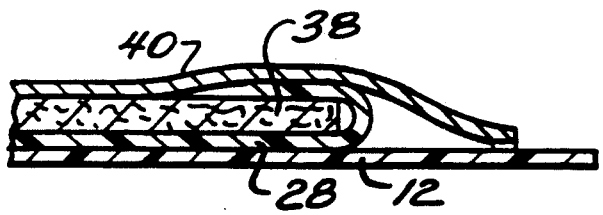
FIG. 11 is a fragmentary sectional view of another embodiment of the present invention.

Another embodiment of the diaper of the present invention is illustrated in FIG. 11, in which like reference numerals designate like parts. In this embodiment, the cover sheet 40 has side dimensions smaller than that of the backing sheet 12, such that the side edges of the cover sheet 40 are spaced inwardly from side edges of the backing sheet 12. In other respects, the diaper of FIG. 11 is similar to that previously described in connection with FIGS. 1-4.

Figure 12:
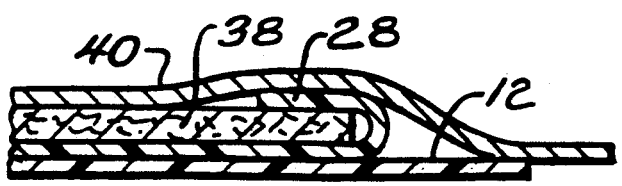
FIG. 12 is a fragmentary sectional view of another embodiment of the present invention.

Another embodiment of the diaper of the present invention is illustrated in FIG. 12, in which like reference numerals designate like parts. In this embodiment, the side dimensions of the backing sheet 12 are smaller than the side dimensions of the cover sheet 40. Thus, the side edges of the backing sheet 12 are located inwardly of the side edges of the cover sheet 40. In other respects, the diaper of FIG. 12 is similar to that previously described in connection with FIGS. 1-4.

The barrier sheet 28 of the diaper 10 may have the same width and length as the diaper 10 if desired. Also, the elastic strips or members 42 may be positioned 0-2 inches from the side edges of the absorbent pad and the cover sheet 40 may be the same size as the backing 12.

Since certain changes may be made without departing from the scope of the invention herein contemplated, it is to be understood that the foregoing description and accompanying drawing shall be taken as illustrative and not in a limiting sense.

I claim:

1. A unitary disposable diaper adapted when worn to engage the waist and stomach areas of the wearer comprising in order:

(1) a liquid impervious back sheet having opposed side edge and opposed end edges connecting the side edges, the back sheet defining the shape and dimensions of the diaper, the diaper having a crotch portion adapted to engage the crotch of the wearer to capture and retain body waste material when the diaper is folded medially and worn engaging the waist and stomach areas, the back sheet having peripheral portions defining an opening in the crotch area;

(2) A liquid-impermeable barrier sheet having opposed side edges and opposed end edges connecting the side edges, the barrier sheet being of substantially the same dimension as the crotch portion, the barrier sheet being of slightly larger dimensions than the opening in the back sheet and being sealed around its periphery in fluid-tight relationship to peripheral edges of the back sheet surrounding the opening in the back sheet; and (3) an absorbent pad adapted for receiving body waste material seated on the free surface of the barrier sheet opposed from the back sheet, the absorbent pad having opposed side and end edges, the absorbent pad being slightly narrower than the barrier sheet, the side edges of the barrier sheet extending around and over the side edges of the pad, thereby providing a barrier against body waste material from escaping through the back of the diaper or through the side edges of the pad.

2. The diaper of claim 1 including a liquid pervious cover sheet covering at least a front surface of the pad.

3. The diaper of claim 2 wherein the side edges of the barrier sheet extending over the pad are secured to an inner surface of the cover sheet.

4. The diaper of claim 2 wherein the cover sheet has substantially the same dimensions as the back sheet, the cover and back sheet being secured together around their common periphery.

5. The diaper of claim 2 wherein the cover sheet is of smaller dimensions than the back sheet, the cover sheet being secured around its periphery to at least one of the back and barrier sheets.

6. The diaper of claim 1 wherein the absorbent pad includes a superabsorbent material.

7. The diaper of claim 1 wherein the barrier sheet extends to the end edges of the back sheet and cover sheet.

* * * * *